United States Patent
Dunn et al.

(10) Patent No.: US 6,930,188 B2
(45) Date of Patent: Aug. 16, 2005

(54) STABLE HYDRATE OF A MUSCARINIC RECEPTOR ANTAGONIST

(75) Inventors: Peter James Dunn, Sandwich (GB); John George Matthews, Sandwich (GB); Trevor Jack Newbury, Sandwich (GB); Garry O'Connor, Sandwich (GB)

(73) Assignee: Novartis International Pharmaceutical, Ltd., Hamilton (BE)

( * ) Notice: Subject to any disclaimer, the term of this patent is extended or adjusted under 35 U.S.C. 154(b) by 22 days.

(21) Appl. No.: 10/396,887

(22) Filed: Mar. 25, 2003

(65) Prior Publication Data

US 2003/0191176 A1 Oct. 9, 2003

Related U.S. Application Data

(60) Provisional application No. 60/374,893, filed on Apr. 23, 2002.

(30) Foreign Application Priority Data

Mar. 26, 2002 (GB) .............................. 0207104

(51) Int. Cl.$^7$ ...................... C07D 307/78; C07D 405/06
(52) U.S. Cl. ...................... 548/525; 549/429; 549/456; 549/462; 549/467; 378/70; 548/400; 548/517
(58) Field of Search ................... 549/429, 456, 549/462, 467; 378/70; 548/517, 525

(56) References Cited

U.S. PATENT DOCUMENTS

| | | | | |
|---|---|---|---|---|
| 5,096,890 A | * | 3/1992 | Cross et al. | 514/422 |
| 5,233,053 A | * | 8/1993 | Cross et al. | 548/568 |
| 5,837,724 A | * | 11/1998 | Allen et al. | 514/422 |
| 6,106,864 A | * | 8/2000 | Dolan et al. | 424/488 |

FOREIGN PATENT DOCUMENTS

| | | | | |
|---|---|---|---|---|
| EP | 0388054 | 11/1993 | | C07D/207/08 |

* cited by examiner

*Primary Examiner*—Golam M M Shameem
(74) *Attorney, Agent, or Firm*—E. Jay Wilusz, Jr.

(57) ABSTRACT

A stable solid hydrate of a muscarinic receptor antagonist is useful in the treatment of irritable bowel syndrome, diverticular disease, oesophageal achalasia, chronic obstructive airways disease, over active bladder (including symptoms of incontinence, urge and frequency), urinary incontinence, neurogenic urinary urgency or pollakiuria, treatment of bladder functional disorder, urinary leakage, painful or difficult urination caused by neurogenic bladder, spastic or hypertonic bladder, dysfunctional bladder syndrome, gastrointestinal disorders including gastrointestinal hyperactivity, and relaxing effect on intestinal smooth muscle cells.

5 Claims, No Drawings

STABLE HYDRATE OF A MUSCARINIC RECEPTOR ANTAGONIST

This application is filed claiming priority to U.S. Provisional Application No. 60/374,893, filed Apr. 23, 2002, and GB Application No. 0207104.1, filed Mar. 26, 2002.

This invention relates to a stable solid hydrate of the muscarinic receptor antagonist (S)-2-{1-[2-(2,3-dihydrobenzofuran-5-yl)ethyl]-3-pyrrolidinyl}-2,2-diphenylacetamide, otherwise known as darifenacin (VII):

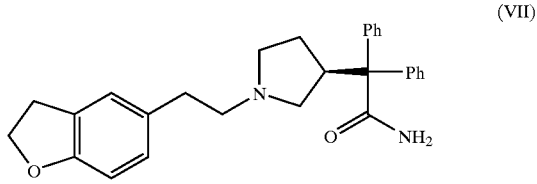

(VII)

In addition, the invention relates to pharmaceutical compositions containing the hydrate of the invention and to uses of said hydrate in medicine. Such pharmaceutical compositions are particularly relevant to the treatment of conditions for which an antagonist of muscarinic receptors is required, such as irritable bowel syndrome, diverticular disease, oesophageal achalasia, chronic obstructive airways disease, over active bladder including symptoms of incontinence, urge and frequency, urinary incontinence, neurogenic urinary urgency or pollakiuria, treatment of bladder functional disorder, urinary leakage, painful or difficult urination caused by neurogenic bladder, spastic or hypertonic bladder, dysfunctional bladder syndrome, gastrointestinal disorders including gastrointestinal hyperactivity, and relaxing effect on intestinal smooth muscle cells.

European patent 0388054 describes a family of 3-substituted pyrrolidine derivatives including darifenacin and pharmaceutically acceptable salts thereof as muscarinic receptor antagonists. The pharmaceutically acceptable salts include acid addition salts, specifically the hydrochloride, hydrobromide, hydrofluoride, sulphate or bisulphate, phosphate or hydrogen phosphate, acetate, besylate, citrate, fumarate, gluconate, lactate, maleate, mesylate, succinate and tartrate salts.

The hydrobromide salt of darifenacin has been the preferred compound for medical usage. The salt is produced from the corresponding anhydrous free base. However, a problem associated with the free base is that it is very unstable, having a shelf life of only one month. Additionally it can be difficult to produce the free base in a sufficiently pure form for pharmaceutical use.

Surprisingly it has been found that this problem can be addressed by synthesising the hydrate of darifenacin for conversion to the hydrobromide salt rather than employing the free base to produce the hydrobromide salt. The solid hydrate has been found to remain stable for well over a year. Furthermore, it may be obtained to a level of purity suitable for pharmaceutical use. Conversion of the solid hydrate to the medicinally useful hydrobromide salt may be achieved via a facile transformation.

Accordingly, the present invention provides a stable solid hydrate of darifenacin. It has been shown by X-ray crystallography that the hydrate of the invention can be isolated as a compound possessing a stoichiometry of from 1:0.6 to 1:1 of darifenacin:water.

More particularly the invention provides a compound of the formula (IX):

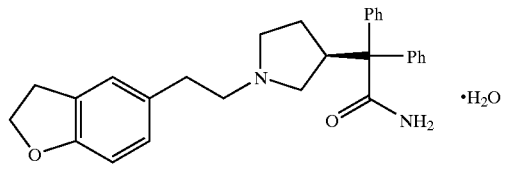

(IX)

In a preferred embodiment a compound of formula (IX) is characterised by an infra-red spectrum, run using single reflection ATR (attenuated total reflectance), which shows significant absorption bands at $v_{max.}$ ($cm^{-1}$): 3625, 3516, 3440, 2948, 2806, 1699, 1622, 1597, 1578, 1488, 1471, 1445, 1378, 1353, 1325, 1312, 1280, 1242, 1196, 1152, 1119, 1102, 1086, 1024, 981, 939, 925, 900.

The compound of formula (IX) can also be characterised by a powder X-ray diffraction pattern obtained using copper radiation ($\lambda$=0.15405 nm) which shows main peaks at 8.39, 10.519, 13.272, 13.693, 15.908, 16.289, 16.855, 19.637, 21.135, 21.55, 21.722, 23.006, and 26.284 degrees 2θ.

It is still further characterised by its differential scanning calorimetry (DSC) trace which shows a sharp endotherm at 101° C. at a scan rate of 20° C./min.

Infra Red spectroscopy was performed using a Nicolet Avatar 360 FT-IR spectrometer. Samples were run using single reflection ATR (attenuated total reflectance) with the spectrometer scanning in a spectral range of 650 $cm^{-1}$ to 4000 $cm^{-1}$.

PXRD data were obtained using a SIEMENS D5000 powder X-ray diffractometer fitted with an automatic sample changer, a theta-theta goniometer, automatic beam divergence slits, a secondary monochromator and a scintillation counter. The samples were prepared for analysis by packing the powder on to silicon wafer specimen mounts. Each specimen was rotated whilst being irradiated with copper K-alpha$_1$ X-rays (wavelength=1.5406 Ångstroms) with the X-ray tube operated at 40 kV/40 mA. The analyses were performed with the goniometer running in step-scan mode set for a 5 second count per 0.02° step over a two theta range of 2° to 45°.

DSC was performed using a Perkin Elmer DSC-7 instrument fitted with an automatic sample changer. Approximately 3 mg of sample was accurately weighed into a 50 microlitre aluminium pan and crimp sealed with a perforated lid. The samples were heated at 20° C./min over the range 40° C. to 250° C. with a nitrogen gas purge.

The invention further provides pharmaceutical compositions comprising a hydrate of the invention, as described above, together with a pharmaceutically acceptable excipient, diluent or carrier.

Additionally, the invention provides the use of a hydrate of the invention, as described above, or of a pharmaceutical composition comprising a hydrate of the invention, as described above, as a medicament.

Still further the invention provides the use of a hydrate of the invention, as described above, or of a pharmaceutical composition comprising a hydrate of the invention, as described above, for the manufacture of a medicament for curative or prophylactic treatment of a medical condition for which an antagonist of muscarinic receptors is indicated. Such conditions are irritable bowel syndrome, diverticular disease, oesophageal achalasia, chronic obstructive airways disease, over active bladder (including symptoms of incontinence, urge and frequency), urinary incontinence, neurogenic urinary urgency or pollakiuria, treatment of bladder functional disorder, urinary leakage, painful or difficult urination caused by neurogenic bladder, spastic or hypertonic bladder, dysfunctional bladder syndrome, gastrointestinal disorders including gastrointestinal hyperactivity, and relaxing effect on intestinal smooth muscle cells.

Also provided by the invention is a method of treatment of a mammal to cure or prevent a medical condition for which an antagonist of muscarinic receptors is indicated, which comprises administering to said mammal an effective amount of a hydrate of the invention, as described above, or an effective amount of a pharmaceutical composition comprising a hydrate of the invention, as described above.

The present invention also includes all suitable isotopic variations of a hydrate of the invention, as described above. An isotopic variation of a hydrate of the invention, as described above, is defined as one in which at least one atom is replaced by an atom having the same atomic number but an atomic mass different from the atomic mass usually found in nature. Examples of isotopes that can be incorporated into a hydrate of the invention, as described above, include isotopes of hydrogen, carbon, nitrogen and oxygen such as $^2$H, $^3$H, $^{13}$C, $^{14}$C, $^{15}$N, $^{17}$O and $^{18}$O respectively. Certain isotopic variations of a hydrate of the invention, as described above, for example, those in which a radioactive isotope such as $^3$H or $^{14}$C is incorporated, are useful in drug and/or substrate tissue distribution studies. Tritiated, i.e. $^3$H, and carbon-14, i.e. $^{14}$C, isotopes are particularly preferred for their ease of preparation and detectability. Further, substitution with isotopes such as deuterium, i.e. $^2$H, may afford certain therapeutic advantages resulting from greater metabolic stability, for example, increased in vivo half-life or reduced dosage requirements and hence may be preferred in some circumstances. Isotopic variations of a hydrate of the invention, as described above, can generally be prepared by conventional procedures such as by the illustrative methods or by the preparations described in the examples and preparations hereafter using appropriate isotopic variations of suitable reagents.

Hydrates of the invention, as described above, can be administered alone but will generally be administered in admixture with a suitable pharmaceutical excipient, diluent or carrier selected with regard to the intended route of administration and standard pharmaceutical practice. For example, a hydrate of the invention, as described above, can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed-, or controlled-release applications. Hydrates of the invention, as described above, may also be administered as fast-dispersing or fast-dissolving dosage forms or in the form of a high energy dispersion or as coated particles. Suitable formulations of a hydrate of the invention, as described above, may be in coated or uncoated form as desired.

Such solid pharmaceutical compositions, for example tablets, may contain excipients such a microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, a hydrate of the invention, as described above, may be combined with various sweetening or flavouring agents, colouring matter or dyes, with emulsifying and/or suspending agents and with diluents such as water, ethanol, propylene glycol and glycerin, and combinations thereof.

Hydrates of the invention, as described above, can also be administered parenterally, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, enough salts of glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the hydrates of the invention, as described above, will usually be from 1.5 to 30 mg (in single or divided doses). The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Hydrates of the invention, as described above, can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a hydrate of the invention, as described above, and a suitable powder base such as lactose or starch.

Aerosol or dry powder formulations are preferably arranged so that each metered dose or "puff" contains from 0.2 mg to 3.0 mg of a hydrate of the invention, as described above, for delivery to the patient. The overall daily dose with an aerosol will be in the range of from 0.5 mg to 10.0 mg of a hydrate of the invention, as described above, which may be administered in a single dose or, more usually, in divided doses throughout the day.

Alternatively, a hydrate of the invention, as described above, can be administered in the form of a suppository or pessary, or it may be applied topically in the form of a gel, hydrogel, lotion, solution, cream, ointment or dusting powder. Hydrates of the invention, as described above, may also be dermally or transdermally administered, for example, by the use of a skin patch. They may also be administered by the pulmonary or rectal routes.

Alternatively, hydrates of the invention, as described above, may be administered topically to the skin, mucosa, dermally or transdermally, for example, in the form of a gel, hydrogel, lotion, solution, cream, ointment, dusting powder, dressing, foam, film, skin patch (for example, but not limited to, the following types, reservoir, matrix, drug-in-adhesive, multilaminate polymer sysytem), wafers, implant, sponges, fibres, bandage, microemulsions and combinations thereof. For such applications, a hydrate of the invention, as described above, can be suspended or dissolved in, for example, a mixture with one or more of the following: mineral oil, liquid petrolatum, white petrolatum, propylene glycol, polyoxyethylene polyoxypropylene compound, emulsifying wax, glycerine, silicone fluids, fixed oils, including synthetic mono- or diglycerides, and fatty acids and fatty acid esters, including oleic acid, water, sorbitan monostearate, a polyethylene glycol, liquid paraffin, polysorbate 60, cetyl esters wax, cetearyl alcohol, 2-octyldodecanol, benzyl alcohol, alcohols such as ethanol. Alternatively, penetration enhancers may be used, for example but not limited to the following in the Journal of Pharm. Sciences, October 1999 by Finnin and Morgan "Transdermal Penetration Engancers: Applications, Limitations and Potential". The following may also be used polymers, carbohydrates, proteins, phospolipids in the form of nanoparticles (such as niosomes or liposomes) or suspended or dissolved. In addition, they may be delivered using iontophoresis, electroporation, phonophoresis, sonophoresis and needle free injections.

Hydrates of the invention, as described above, may also be used in combination with a cyclodextrin. Cyclodextrins are known to form inclusion and non-inclusion complexes with drug molecules. Formation of a drug-cyclodextrin complex may modify the solubility, dissolution rate, bioavailabilty and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

The compounds of the invention may be prepared as shown below:

Scheme 1.
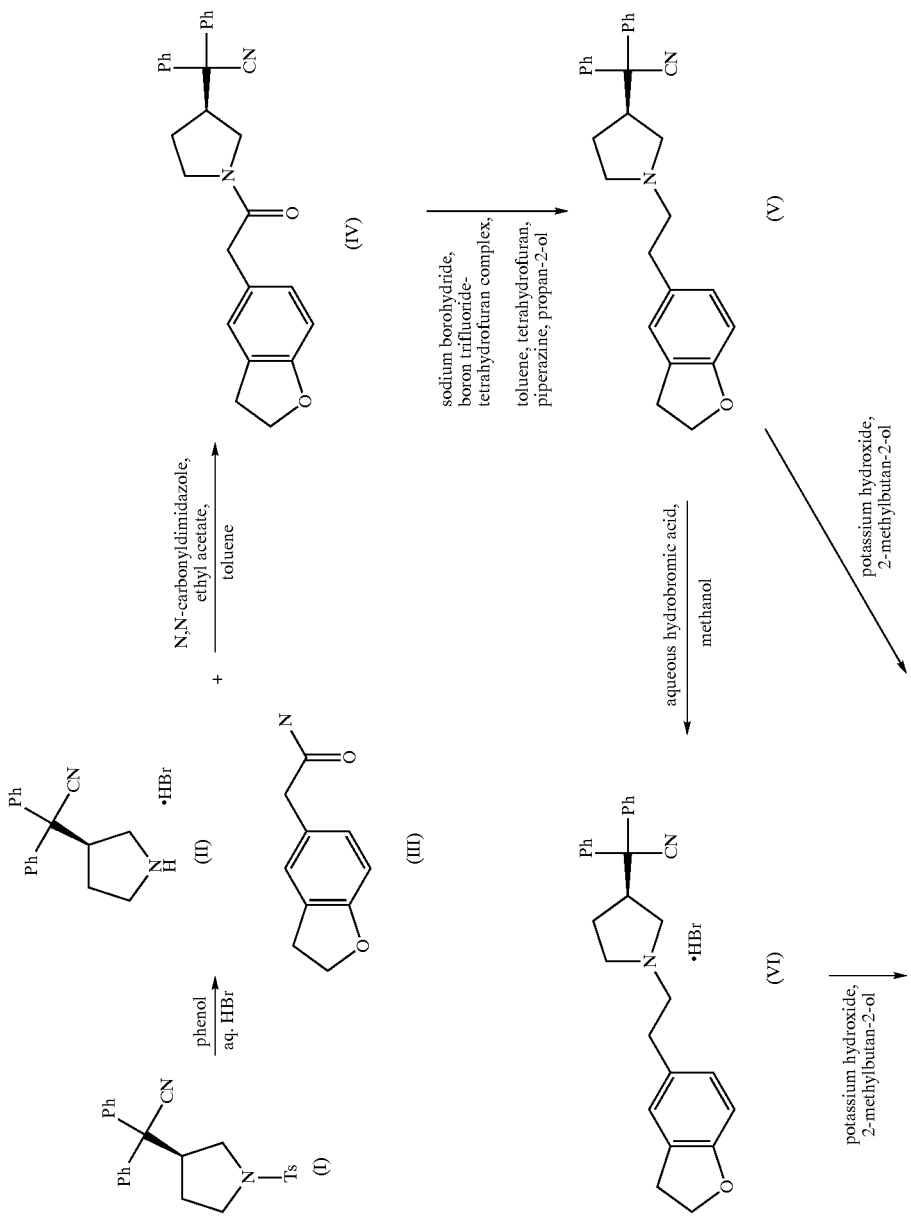

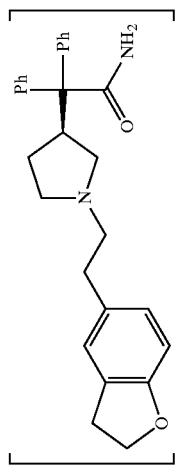
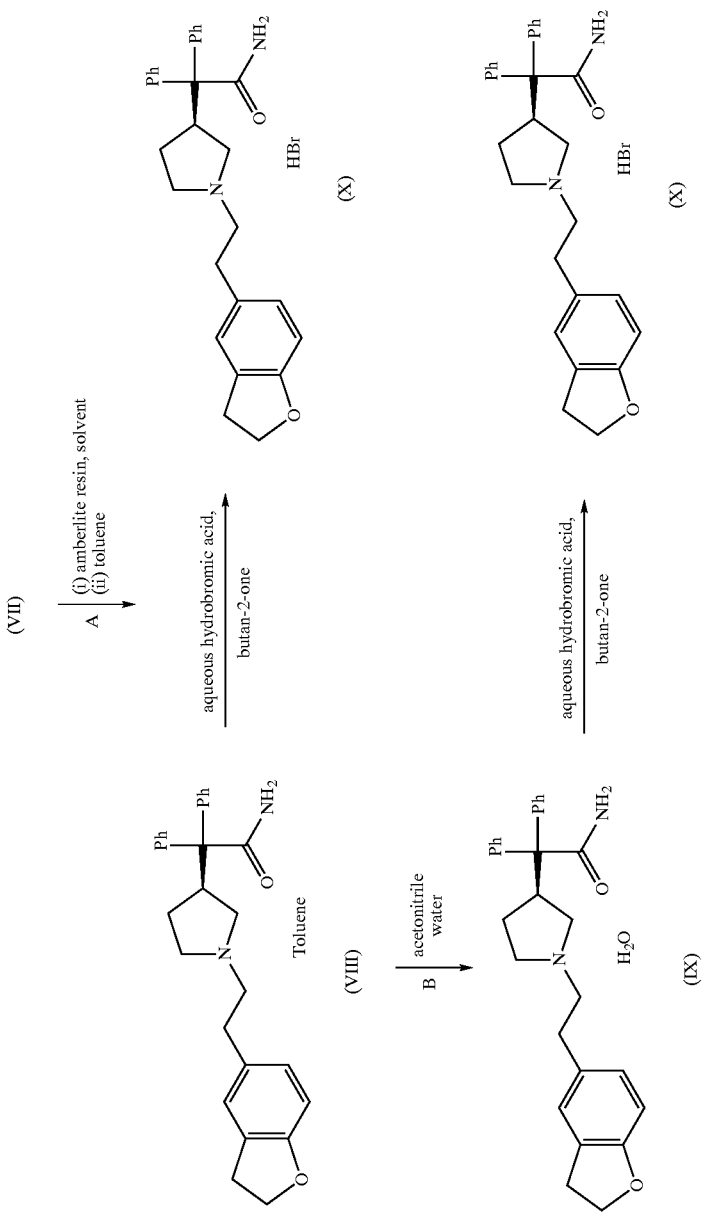

Surprisingly it has been found that darifenacin hydrate may be obtained in a pharmaceutically pure form from a solution of darifenacin which is subjected to a resin treatment and then converted to the hydrate via a toluene solvate (see steps A and B in Scheme 1.). Darifenacin toluene solvate may be directly converted to the hydrobromide, however this conversion does not allow for flexibility in the production plant scheduling because the toluene solvate is not stable over medium to long term storage periods. This additional burden on the manufacturing process may be overcome by converting darifenacin toluene solvate to darifenacin hydrate, which is stable over long periods, and so conversion to darifenacin hydrobromide can then be performed when required without fear that in the meantime compound (IX) will have degraded in quality.

Accordingly, the present invention further provides a process for providing a hydrate of the invention, as described above, in pharmaceutically pure form by subjecting darifenacin to a resin treatment followed by conversion to a toluene solvate which is in turn converted to said hydrate. A solution of darifenacin in a suitable organic solvent or aqueous organic solvent mixture is combined with the resin and the resulting mixture is stirred at between ambient temperature and reflux. Subsequently the darifenacin solution is separated from the resin by filtration. Preferably the resin is a quaternary ammonium hydroxide resin. The resin treatment may be performed in batch mode or in a continuous processing mode. The hydrate may be further elaborated to give an acid addition salt of darifenacin. Preferably, the acid addition salt is the hydrobromide salt.

Further, the present invention provides a novel intermediate for the provision of a hydrate of the invention, as described above, in the form of the toluene solvate of darifenacin. It is envisaged that other solvates of darifenacin, for example the ethyl acetate solvate, may be employed in the place of the toluene solvate.

It has been shown by X-ray crystallography that compound (VIII) possesses a 1:1 stoichiometry, i.e. one molecule of darifenacin and one molecule of toluene in an asymmetric unit.

Compound of formula (VIII) is characterised by an infrared spectrum, run using single reflection ATR (attenuated total reflectance), which shows significant absorption bands at $v_{max}$ (cm$^{-1}$): 3463, 3342, 3299, 3285, 3022, 2925, 2825, 1673, 1614, 1490, 1440, 1384, 1333, 1319, 1243, 1195, 1152, 1130, 1115, 1102, 1028, 1003, 980, 939, 926, 907.

This compound can also be characterised by a powder X-ray diffraction pattern obtained using copper radiation ($\lambda$=0.15405 nm) which shows main peaks at 12.572, 12.754, 15.978, 17.419, 18.537, 18.889, 20.78, 21.562, 22.437, 22.736, 23.767, 24.075, 24.266, 25.35, 25.762, 27.214, and 29.716 degrees 2θ.

It is still further characterised by its differential scanning calorimetry (DSC) trace which shows a sharp endotherm at 92° C. at a scan rate of 20° C./min.

The following examples illustrate the preparation of compounds disclosed in Scheme 1.:

EXAMPLE 1

(S)-2,2-diphenyl-2-(3-pyrrolidinyl)acetonitrile hydrobromide (II)

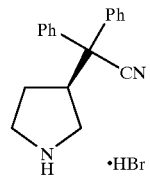

A mixture of (S)-2,2-diphenyl-2-(1-tosyl-3-pyrrolidinyl)acetonitrile (I) [see European Patent Publication No. 0388054] (83.8 Kg, 201.2 moles), 48% aqueous hydrobromic acid (419 L, 5 L/Kg of compound I) and phenol (16.8 Kg, 0.2 Kg/Kg of compound I) is heated at reflux for 3 hours. The mixture is cooled and extracted with dichloromethane (1×560 Kg, 1×523 Kg). The extracts are combined and washed with aqueous sodium chloride solution (15 Kg in 150 Kg of water). The organic layer is concentrated and essentially replaced with ethyl acetate to a total volume of about 440 L. Hexane (276 Kg) is added at 40° C. and product is collected at 0–5° C. by filtration. The (S)-2,2-diphenyl -2-(3-pyrrolidinyl)acetonitrile hydrobromide is washed with chilled ethyl acetate and dried under vacuum at 60° C. Yield 52.8 Kg (76%).

$v$=3441, 2940, 2745, 2455, 2246, 1972, 1886, 1806, 1596, 1585, 1561, 1494, 1450, 1392, 1289, 1255, 1217, 1159, 1104, 1070, 1034, 1002, 967, 917, 899, 833, 766, 750, 702, 664, 645, 546, 496, 472 cm$^{-1}$.

$^1$H NMR (300 MHz, CDCl$_3$): δ=2.12 (2H, m), 3.15 (1H, m), 2.96 (3H, m), 3.76 (1H, quin, J 8 Hz), 7.25–7.41 (6H, m), 7.47 (4H, t, J 8 Hz), 9.23 (1H, br. s), 9.43 (1H, br). LRMS (electrospray, positive ion): m/z [MH$^+$] 263.

Optical rotation: $[\alpha]_{365}^{25}$=−55.9°

EXAMPLE 2

(S)-3-(cyanodiphenylmethyl)-1-[2-(2,3-dihydrobenzofuran-5-yl)acetyl]pyrrolidine (IV)

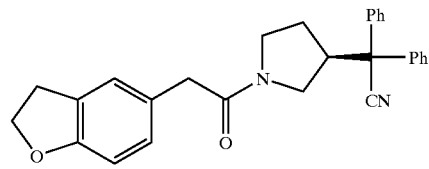

To a cooled (0–5° C.) slurry of 2-(2,3-dihydrobenzofuran-5-yl)acetic acid (III) (9.85 Kg, 55.3 moles) in ethyl acetate (115 L) is added carbonyldiimidazole (8.97 Kg, 55.3 moles). The reaction is stirred at 5–10° C. for 1 hour prior to the addition of (S)-2,2-diphenyl-2-(3-pyrrolidinyl)acetonitrile hydrobromide (II) (17.25 Kg, 50.2 moles). The reaction is allowed to warm up to 20–25° C. and stirred for an additional 3 hours. The reaction mixture is washed with 2N aqueous hydrochloric acid (42 L) then aqueous sodium bicarbonate (2.1 Kg in 42 L of water). The ethyl acetate solution is concentrated and essentially replaced with toluene to furnish a solution of product in toluene with a total volume of about 43 L. The assumed yield of (S)-3-(cyanodiphenylmethyl)-1-[2-(2,3-dihydrobenzofuran-5-yl)acetyl]pyrrolidine is 100% (21.2 Kg) and is employed directly in the preparation of compound V.

ν=3448, 3059, 3026, 2973, 2948, 2878, 2236, 1959, 1890, 1811, 1719, 1643, 1600, 1491, 1449, 1421, 1362, 1336, 1297, 1241, 1219, 1198, 1159, 1125, 1102, 1034, 1002, 983, 944, 917, 892, 836, 804, 764, 752, 701, 667, 646, 618, 576, 550, 469, 424, 405 cm$^{-1}$.

For this compound, two structural conformations exist giving rise to 'doubled-up' signals for some of the resonances. $^1$H NMR (300 MHz, CDCl$_3$): δ=1.85–2.20 (2H, m), 3.16 & 3.18 (2H, t, J 9 Hz), 3.20–3.85 (7H, m), 4.54 & 4.55 (2H, t, J 9 Hz), 6.68 & 6.70 (1H, d, J 9 Hz), 6.83 & 6.94 (1H, d, J 9 Hz), 7.05 & 7.12 (1H, s), 7.22–7.48 (10H, m).

LRMS (electrospray, positive ion): m/z [MH$^+$] 423.

Optical rotation: [α]$_{365}^{25}$=+85.9°

EXAMPLE 3

(S)-2-{1-[2-(2,3-dihydrobenzofuran-5-yl)ethyl]-3-pyrrolidinyl}-2,2-diphenylacetonitrile (V)

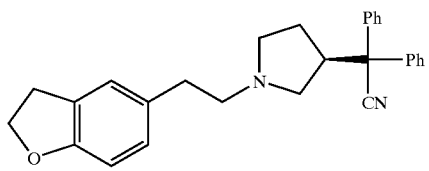

To a cooled (0° C.) mixture of (S)-3-(cyanodiphenylmethyl)-1-[2-(2,3-dihydrobenzofuran-5-yl)acetyl]pyrrolidine (IV) as a toluene solution (7.43 Kg active, 17.59 moles) and sodium borohydride (0.87 Kg, 23 moles) in tetrahydrofuran (29.7 L) is added boron trifluoride tetrahydrofuran complex (4.31 Kg, 30.81 moles) at such a rate as to maintain the temperature of the reaction below 10° C. The reaction is warmed to ambient temperature and stirred for a further 4 hours. Aqueous piperazine solution is added and the mixture is heated at reflux for 8 hours. The aqueous layer is separated and washed with 1% aqueous sodium chloride solution (22.3 L) at 40° C. The organic layer is concentrated and essentially replaced by isopropyl alcohol at atmospheric pressure to a total volume of about 30 L. The product crystallises on cooling and is collected at 0–5° C. by filtration. (S)-2-{1-[2-(2,3-dihydrobenzofuran-5-yl)ethyl]-3-pyrrolidinyl}-2,2-diphenylacetonitrile (V) is washed with chilled isopropyl alcohol and dried under vacuum at 50° C. Yield 6.34 Kg (88%).

ν=3441, 3088, 3056, 3032, 2947, 2924, 2884, 2856, 2790, 2744, 2237, 1955, 1883, 1809, 1614, 1596, 1489, 1448, 1385, 1353, 1338, 1322, 1290, 1245, 1216, 1195, 1148, 1130, 1101, 1076, 1033, 1016, 1003, 980, 944, 921, 891, 847, 819, 799, 764, 750, 701, 674, 658, 646, 573, 563, 540, 504, 491, 427, 403 cm$^{-1}$.

$^1$H NMR (300 MHz, CDCl$_3$); 1.86 (1H, m), 2.10 (1H, m), 2.38 (1H, t, J 9 Hz), 2.52 (1H, q, J 8 Hz), 2.59–2.75 (4H, m), 2.84 (1H, m), 3.02 (1H, dt, J 4 & 9 Hz), 3.16 (2H, t, J 9 Hz), 3.47 (1H, m), 4.53 (2H, t, J 9 Hz), 6.67 (1H, d, J 8 Hz), 6.90 (1H, d, J 8 Hz), 7.00 (1H, s), 7.23–7.40, (6H, m), 7.46 (4H, t, J 8 Hz).

LRMS (electrospray, positive ion): m/z [MH$^+$] 409.

Optical rotation: [α]$_{365}^{25}$=+31.8°

EXAMPLE 4

(S)-2-{1-[2-(2,3-dihydrobenzofuran-5-yl)ethyl]-3-pyrrolidinyl}-2,2-diphenylacetonitrile hydrobromide (VI)

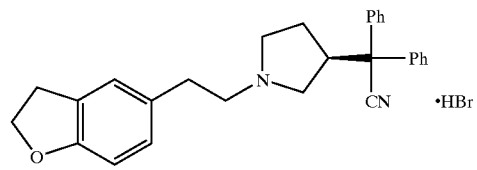

To a slurry of (S)-2-{1-[2-(2,3-dihydrobenzofuran-5-yl)ethyl]-3-pyrrolidinyl}-2,2-diphenylacetonitrile (V) (30.0 g, 0.073 moles) in methanol (150 mL) is added 48% aqueous hydrobromic acid (13.6 g, 0.081 moles) maintaining the temperature below 40° C. The mixture is heated at reflux for 1 hour. The batch is cooled to 0° C., and the product is collected by filtration, washed with methanol (60 mL) and dried at 50° C. under vacuum to give (S)-2-{1-[2-(2,3-dihydrobenzofuran-5-yl)ethyl]-3-pyrrolidinyl}-2,2-diphenylacetonitrile hydrobromide (VI) (33.5 g, 93%).

ν=3440, 3059, 3002, 2931, 2893, 2856, 2653, 2624, 2548, 2496, 2471, 2239, 1960, 1888, 1812, 1615, 1599, 1493, 1450, 1394, 1363, 1332, 1294, 1242, 1159, 1129, 1106, 1088, 1073, 1035, 1003, 981, 941, 889, 830, 766, 751, 725, 703, 666, 645, 582, 548, 534, 500, 476, 423 cm$^{-1}$.

$^1$H NMR (300 MHz, CDCl$_3$); 2.08 (1H, m), 2.46 (1H, m), 2.75 (1H, q, J 10 Hz), 2.69–3.33 (7H, m), 3.70 (1H, m), 3.83 (1H, m), 4.09 (1H, m), 4.54 (2H, t, J 9 Hz), 6.69 (1H, d, J8 Hz), 6.92 (1H, d, J8 Hz), 7.06 (1H, s), 7.27–7.50 (10H, m), 12.08 (1H, br).

LRMS (electrospray, positive ion): m/z [MH$^+$] 409.

Optical rotation: [α]$_{365}^{25}$=+90.0°

EXAMPLE 5

(S)-2-{1-[2-(2,3-dihydrobenzofuran-5-yl)ethyl]-3-pyrrolidinyl}-2,2-diphenylacetamide toluene solvate (VIII)

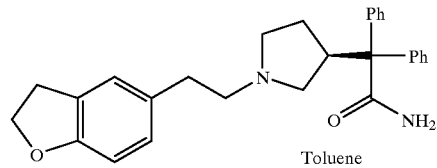

Method 1: A slurry of potassium hydroxide (48.7 g, 0.87 moles) in 2-methylbutan-2-ol (175 mL) is heated at 50–60° C. After 1 hour (S)-2-{1-[2-(2,3-dihydrobenzofuran-5-yl)ethyl]-3-pyrrolidinyl}-2,2-diphenylacetonitrile hydrobromide (VI) (25.0 g, 0.051 moles) is added and the resulting mixture is heated at reflux for 20 hours. The reaction mixture is cooled to ambient temperature and water (125 mL) is added maintaining the temperature below 30° C. The mixture is stirred for 15 minutes, then allowed to settle and the organic phase is separated. The organic phase is washed with aqueous sodium chloride (125 mL of 5% w/w solution) to provide a solution of (S)-2-{1-[2-(2,3-dihydrobenzofuran-5-yl)ethyl]-3-pyrrolidinyl}-2,2-diphenylacetamide as a solution in 2-methylbutan-2-ol (VII). The solution is heated at reflux in the presence of Amberlite® resin (37.5 g) for 22 hours then cooled to ambient temperature. The Amberlite® resin is removed by filtration and washed with 2-methylbutan-2-ol (25 mL). The combined 2-methylbutan-2-ol phases are concentrated and essentially replaced by toluene to a final volume of approximately 140 mL. The toluene solution is cooled to 0° C. during which time crystallisation occurs. (S)-2-{1-[2-(2,3-dihydrobenzofuran-5-yl)ethyl]-3-pyrrolidinyl}-2,2-diphenylacetamide toluene solvate (VIII) is collected by filtration, washed with chilled toluene (25 mL) and dried at 35° C. under vacuum. Yield (22.2 g, 84%).

Method 2: A slurry of potassium hydroxide (40 g, 0.71 moles) in 2-methylbutan-2-ol (140 mL) is heated at 50–60° C. After 1 hour, (S)-2-{1-[2-(2,3-dihydrobenzofuran-5yl)ethyl]-3-pyrrolidinyl}-2,2-diphenylacetonitrile (V) (20 g, 0.049 moles) is added and the resulting mixture is heated at reflux for approximately 20 hours. The reaction mixture is cooled and water (100 mL) is added maintaining the temperature below 34° C. The mixture is stirred for 30 minutes and the organic phase is separated. The organic phase is washed with aqueous sodium chloride (100 mL of 5% w/w solution) to provide a solution of the product as a solution in 2-methylbutan-2-ol. The solution is heated at reflux in the presence of Amberlite® resin (30 g) for 9 hours then cooled to ambient temperature. The Amberlite® resin is removed by filtration and washed with 2-methylbutan-2-ol (20 mL). The combined 2-methylbutan-2-ol phases are concentrated and essentially replaced by toluene to a final volume of approximately 80 mL. The toluene solution is cooled to 0° C. during which time crystallisation occurs. (S)-2-{1-[2-(2,3-dihydrobenzofuran-5-yl)ethyl]-3-pyrrolidinyl}-2,2-diphenylacetamide toluene solvate (VIII) is collected by filtration, washed with toluene (70 mL) and dried at 35° C. under vacuum. Yield (17.2 g, 68%).

ν=3463, 3342, 3299, 3285, 3022, 2925, 2825, 1673, 1614, 1490, 1440, 1384, 1333, 1319, 1243, 1195, 1152, 1130, 1115, 1102, 1028, 1003, 980, 939, 926, 907 cm$^{-1}$.

$^1$H NMR (300 MHz, d$^6$-DMSO): δ=1.57 (1H, m), 1.93 (2H, m), 2.3–2.5 (6H, m), 2.82 (1H, t, J 9), 3.11 (2H, t, J 9), 3.62 (1H, m), 4.47 (2H, t, J 9), 6.62 (1H, d, J 8),6.82 (1H, d, J 8), 6.99 (1H, s), 7.08 (2H, m), 7.2–7.4 (10H, m). Signals were observed for toluene corresponding to a molar ratio of 1 at 2.3 and are present underneath the aromatic region for (S)-2-{1-[2-(2,3-dihydrobenzofuran-5-yl)ethyl]-3-pyrrolidinyl}-2,2-diphenylacetamide.

Optical rotation: $[\alpha]_{365}^{25}$=119.0°

EXAMPLE 6

(S)-2-{1-[2-(2,3-dihydrobenzofuran-5-yl)ethyl]-3-pyrrolidinyl}-2,2-diphenylacetamide hydrate (IX)

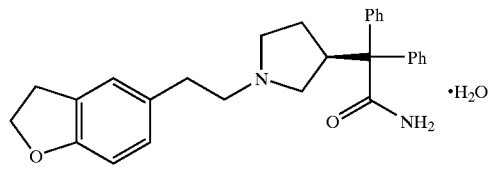

A solution of (S)-2-{1-[2-(2,3-dihydrobenzofuran-5-yl)ethyl]-3-pyrrolidinyl}-2,2-diphenylacetamide toluene solvate (VIII) (16 g, 0.031 moles) in acetonitrile (320 mL) is concentrated under reduced pressure at ambient temperature. The resulting foam is dissolved in acetonitrile (48 mL) to which is added water (1.1 mL) dropwise at ambient temperature. The solution is stirred at ambient temperature until crystallisation occurs and is allowed to stir overnight. The (S)-2-{1-[2-(2,3-dihydrobenzofuran-5-yl)ethyl]-3-pyrrolidinyl}-2,2-diphenylacetamide hydrate (IX) is collected by filtration and dried under vacuum at ambient temperature. Yield (10.4 g, 76%).

ν=3625, 3516, 3440, 2948, 2806, 1699, 1622, 1597, 1578, 1488, 1471, 1445, 1378, 1353, 1325, 1312, 1280, 1242, 1196, 1152, 1119, 1102, 1086, 1024, 981, 939, 925, 900 cm$^{-1}$.

$^1$H NMR (300 MHz, d$^6$-DMSO): δ=1.57 (1H, m), 1.93 (2H, m), 2.3–2.5 (6H, m), 2.82 (1H, t, J 9), 3.11 (2H, t, J 9), 3.62 (1H, m), 4.46 (2H, t, J 9), 6.62 (1H, d, J 8), 6.81 (1H, d, J 8), 6.99 (1H, s), 7.07 (2H, m), 7.2–7.4 (10H, m).

Water content by Karl Fischer: 2.7% w/w

Optical rotation: $[\alpha]_{365}^{25}$=−120.7°

EXAMPLE 7

(S)-2-{1-[2-(2,3-dihydrobenzofuran-5-yl)ethyl]-3-pyrrolidinyl}-2,2-diphenylacetamide hydrobromide (X)

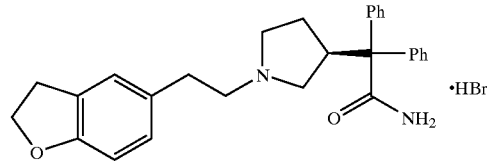

Method 1: A solution of (S)-2-{1-[-2-(2,3-dihydrobenzofuran-5-yl)ethyl]-3-pyrrolidinyl}-2,2-diphenylacetamide toluene solvate (VIII) (30.4 g, 0.059 moles) in butan-2-one (213 mL) is warmed to 33° C. to attain solution and then cooled to 15° C. 48% aqueous hydrobromic acid(9.9 g, 0.059 moles) is then added and the mixture stirred at 15° C. for 1 hour and 0° C. for 2 hours. The (S)-2-{1-[2-(2,3-dihydrobenzofuran-5-yl)ethyl]-3-pyrrolidinyl}-2,2-diphenylacetamide hydrobromide (X) is collected by filtration, washed with butan-2-one (65 mL) and dried under vacuum at 50° C. for 18 hours. Yield (24.6 g, 83%).

Method 2: To a solution of (S)-2-{1-[2-(2,3-dihydrobenzofuran-5-yl)ethyl]-3-pyrrolidinyl}-2,2-diphenylacetamide hydrate (IX) (3.60 g, 0.0081 moles) in butan-2-one (30 mL) is added 48% aqueous hydrobromic acid(1.36 g, 0.0081 moles). The mixture is stirred at 20° C. for 1 hour and 0° C. for 1 hours and the (S)-2-{1-[2-(2,3-dihydrobenzofuran-5-yl)ethyl]-3-pyrrolidinyl}-2,2-diphenylacetamide hydrobromide (X) is collected by filtration, washed with butan-2-one (10 mL) and dried under vacuum at 50° C. for 18 hours. Yield (3.90 g, 95%). m.p.=232° C.

ν=3468, 3211, 3052, 2995, 2870, 2693, 2586, 1668, 1585, 1492, 1442, 1243, 983, 850 cm$^{-1}$.

1H NMR (300 MHz, CDCl3): δ=2.10–2.23 (1H, m); 2.81–2.99 (2H, m); 3.00–3.15 (4H, m); 3.15 (2H, t); 3.18–3.29 (1H, m); 3.48 (1H, t); 3.69 (1H, s); 3.80–3.95 (1H, m); 4.52 (2H, t); 5.58 (1H, bs); 5.62 (1H, bs); 6.63 (1H, d); 6.84 (1H, d); 6.84 (1H, d); 7.01 (1H, s); 7.19–7.40 (10H, m); 11.48 (1H, bs).

Optical rotation: $[\alpha]_{365}^{25}$=+46.0°

What is claimed is:

1. A solvate of darifenacin of the formula (VIII):

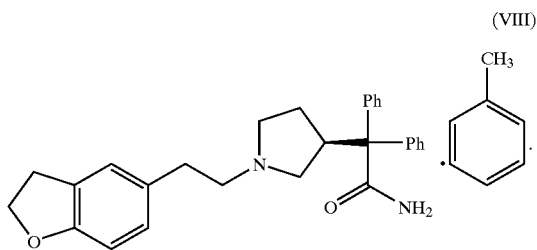

(VIII)

2. A solvate according to claim 1 characterised by an infra-red spectrum, run using single reflection ATR (attenuated total reflectance), which shows significant absorption bands at $v_{max}$(cm$^{-1}$): 3463, 3342, 3299, 3285, 3022, 2925, 2825, 1673, 1614, 1490, 1440, 1384, 1333, 1319, 1243, 1195, 1152, 1130, 1115, 1102, 1028, 1003, 980, 939, 926, 907.

3. A solvate according to claim 1 which is characterised by a powder X-ray diffraction pattern obtained using copper radiation ($\lambda$=0.15405 nm) which shows main peaks at 12.572, 12.754, 15.978, 17.419, 18.537, 18.889, 20.78, 21.562, 22.437, 22.736, 23.767, 24.075, 24.266, 25.35, 25.762, 27.214, and 29.716 degrees 2$\theta$.

4. A solvate according to any of claims 1 which is characterised by a scanning calorimetry (DSC) trace which shows a sharp endotherm at 92° C. at a scan rate of 20° C./min.

5. A process for providing a solvate of formula (VIII) according to claim 1, comprising subjecting (S)-2-{1-[2-(2,3-dihydrobenzofuran-5-yl)ethyl]-3-pyrrolidinyl}-2,2-diphenylacetamide to an ion-exchange resin treatment followed by mixing with toluene.

* * * * *